US008569076B2

(12) United States Patent
Wardlaw et al.

(10) Patent No.: US 8,569,076 B2
(45) Date of Patent: Oct. 29, 2013

(54) METHOD FOR SEROLOGIC AGGLUTINATION AND OTHER IMMUNOASSAYS PERFORMED IN A THIN FILM FLUID SAMPLE

(75) Inventors: Stephen C. Wardlaw, Lyme, CT (US); Robert A. Levine, Guilford, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 501 days.

(21) Appl. No.: 12/417,353

(22) Filed: Apr. 2, 2009

(65) Prior Publication Data
US 2009/0253218 A1    Oct. 8, 2009

Related U.S. Application Data

(60) Provisional application No. 61/041,784, filed on Apr. 2, 2008, provisional application No. 61/041,791, filed on Apr. 2, 2008, provisional application No. 61/041,790, filed on Apr. 2, 2008, provisional application No. 61/041,794, filed on Apr. 2, 2008, provisional application No. 61/041,797, filed on Apr. 2, 2008, provisional application No. 61/043,571, filed on Apr. 9, 2008.

(51) Int. Cl.
*G01N 33/543* (2006.01)
(52) U.S. Cl.
USPC ........... 436/523; 436/518; 436/536; 436/164; 436/807
(58) Field of Classification Search
USPC .................... 436/518, 523, 536, 164, 807
See application file for complete search history.

(56) References Cited

U.S. PATENT DOCUMENTS

| | | | |
|---|---|---|---|
| 4,023,716 A | | 5/1977 | Shapiro |
| 4,197,088 A | | 4/1980 | Meserol et al. |
| 4,487,081 A | | 12/1984 | DeVaughn et al. |
| 4,596,695 A | * | 6/1986 | Cottingham .................. 422/401 |
| 4,615,878 A | | 10/1986 | Kass |
| 4,745,075 A | * | 5/1988 | Hadfield et al. .............. 436/523 |
| 5,012,818 A | | 5/1991 | Joishy |
| 5,066,465 A | * | 11/1991 | Kano et al. .................... 422/412 |
| 5,068,181 A | | 11/1991 | Driscoll |
| 5,188,968 A | * | 2/1993 | Kano et al. .................... 422/412 |
| 5,192,511 A | | 3/1993 | Roach |
| 5,248,479 A | * | 9/1993 | Parsons et al. ................. 422/412 |

(Continued)

FOREIGN PATENT DOCUMENTS

| | | |
|---|---|---|
| DE | 10011235 | 9/2001 |
| DE | 10240742 | 3/2004 |

(Continued)

OTHER PUBLICATIONS

Fan at al., "Integrated barcode chips for rapid, multiplexed analysis of proteins in microliter quantites of blood," Nature Publishing Group, http://www.nature.com/naturebiotechnology, pp. 1-6, Nov. 2008.

(Continued)

*Primary Examiner* — Melanie Y Brown
(74) *Attorney, Agent, or Firm* — O'Shea Getz P.C.

(57) ABSTRACT

A method and system for performing a serological agglutination assay in a liquid sample. The system provides a simple method for creating an in-situ sample/reagent admixture within a sample analysis chamber without the use of any precision fluid-handling components.

5 Claims, 4 Drawing Sheets

(56) References Cited

U.S. PATENT DOCUMENTS

| | | | |
|---|---|---|---|
| 5,270,166 | A | 12/1993 | Parsons et al. |
| 5,284,771 | A | 2/1994 | Fan et al. |
| 5,342,790 | A | 8/1994 | Levine et al. |
| 5,360,719 | A | 11/1994 | Levine et al. |
| 5,447,838 | A | 9/1995 | Meiklejohn et al. |
| 5,454,268 | A | 10/1995 | Kim |
| 5,460,782 | A | 10/1995 | Coleman et al. |
| 5,460,979 | A | 10/1995 | Levine et al. |
| 5,480,778 | A | 1/1996 | Levine et al. |
| 5,593,848 | A | 1/1997 | Levine et al. |
| 5,635,362 | A | 6/1997 | Levine et al. |
| 5,739,042 | A | 4/1998 | Frengen |
| 5,759,794 | A | 6/1998 | Levine et al. |
| 5,768,407 | A | 6/1998 | Shen et al. |
| 5,770,160 | A | 6/1998 | Smith et al. |
| 5,776,710 | A | 7/1998 | Levine et al. |
| 5,834,217 | A | 11/1998 | Levine et al. |
| 5,858,648 | A * | 1/1999 | Steel et al. .......... 435/5 |
| 6,127,184 | A | 10/2000 | Wardlaw |
| 6,235,536 | B1 | 5/2001 | Wardlaw |
| 6,723,290 | B1 | 4/2004 | Wardlaw |
| 6,730,521 | B1 | 5/2004 | Cassells |
| 6,866,823 | B2 | 3/2005 | Wardlaw |
| 6,869,570 | B2 | 3/2005 | Wardlaw |
| 6,929,953 | B1 | 8/2005 | Wardlaw |
| 2002/0028158 | A1 | 3/2002 | Wardlaw |
| 2002/0131902 | A1 | 9/2002 | Levy |
| 2003/0025896 | A1 | 2/2003 | Oever et al. |
| 2003/0224534 | A1 | 12/2003 | Kawate |
| 2004/0048330 | A1 | 3/2004 | Bittner |
| 2004/0165090 | A1 | 8/2004 | Ning |
| 2005/0002826 | A1 | 1/2005 | Oguni et al. |
| 2005/0026197 | A1 | 2/2005 | Dertinger |
| 2005/0277159 | A1 | 12/2005 | Lehmann et al. |
| 2006/0159962 | A1 | 7/2006 | Chandler et al. |
| 2006/0258018 | A1 | 11/2006 | Curl et al. |
| 2007/0087442 | A1 | 4/2007 | Wardlaw |
| 2007/0243117 | A1 | 10/2007 | Wardlaw |
| 2008/0070317 | A1 | 3/2008 | Bradshaw et al. |
| 2009/0041630 | A1 | 2/2009 | Hirabayashi et al. |
| 2009/0191641 | A1 * | 7/2009 | Chiapperi et al. .......... 436/69 |

FOREIGN PATENT DOCUMENTS

| | | | |
|---|---|---|---|
| EP | 0366151 | 5/1990 | .......... 33/543 |
| EP | 0642829 | 3/1995 | |
| EP | 1239284 | 9/2002 | .......... 33/53 |
| EP | 1365240 | 11/2003 | |
| GB | 2254414 | 10/1992 | .......... 21/84 |
| JP | 55080054 | 6/1980 | |
| JP | 02-118453 | 5/1990 | |
| JP | 03-216554 | 9/1991 | |
| JP | 06-11508 | 1/1994 | |
| WO | WO 9802727 | 1/1998 | .......... 15/14 |
| WO | WO 0057891 | 5/2000 | |
| WO | WO 0223154 | 3/2002 | .......... 33/558 |

OTHER PUBLICATIONS

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry," The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optical aggregometry (type born) and flow cytometry in evaluating ADP-induced platelet activation," Cytometry, Part B, Clinical Cytometry, vol. 74, No. 1, pp. 30-39, Jan. 2008.

EP Search Report for EP 097290936 dated Aug. 24, 2012.

Japanese Office Action dated Feb. 28, 2012.

* cited by examiner

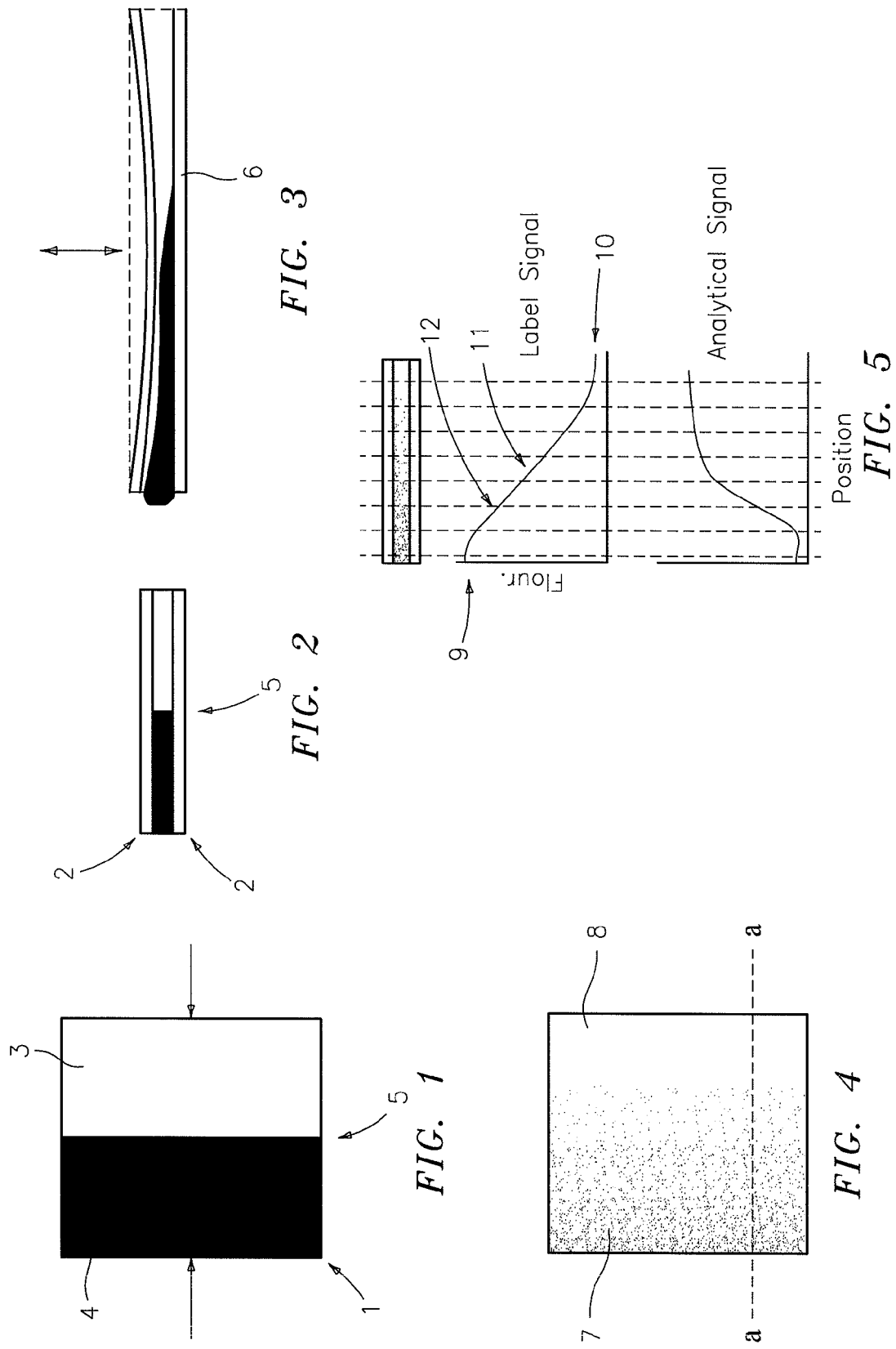

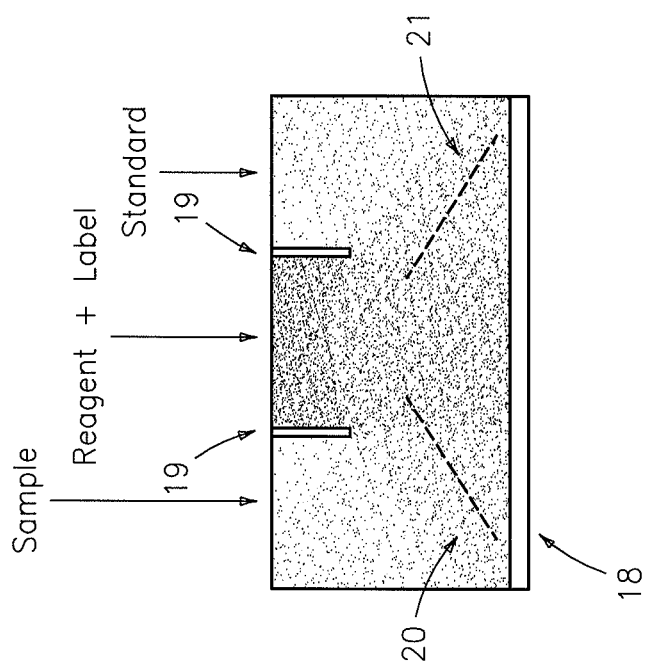
*FIG. 9*
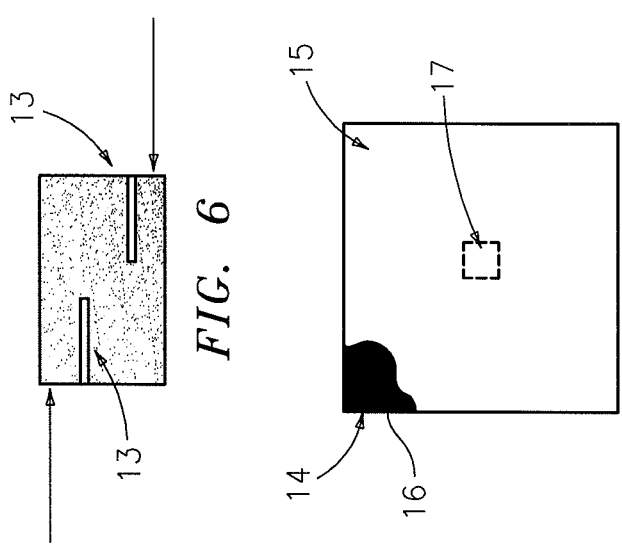
*FIG. 6*
*FIG. 7*
*FIG. 8*

METHOD FOR SEROLOGIC AGGLUTINATION AND OTHER IMMUNOASSAYS PERFORMED IN A THIN FILM FLUID SAMPLE

This application claims the benefit of U.S. Provisional Application Nos.: 61/041,784, filed Apr. 2, 2008; 61/041,791, filed Apr. 2, 2008; 61/041,790, filed Apr. 2, 2008; 61/041,794, filed Apr. 2, 2008; 61/041,797, filed Apr. 2, 2008; and 61/043,571, filed Apr. 9, 2008.

BACKGROUND OF THE INVENTION

1. Technical Field

This disclosure relates to a method and system for performing a serological agglutination assay in a liquid sample. The system provides a simple method for creating an in-situ sample/reagent admixture within a sample analysis chamber without the use of any precision fluid-handling components. The relative and absolute concentrations of the reactants may be ascertained in any small area of the reaction vessel.

2. Background Information

In most assays it is necessary to provide an exact dilution of the sample to be analyzed so that the concentration of the analyte can be brought into the useful range of the assay, and since this dilution affects the concentration of the analyte, the precision and accuracy of the test to a large extent depends upon the precision and accuracy of the dilution. One reason for this dilution is that immunoassays are affected by a phenomenon known as the prozone effect. The term "prozone" as used in this disclosure shall refer to conditions of antibody excess where generally in precipitation or agglutination-based immunoassays reactions are inhibited or prevented, the postzone, where conditions of antigen excess in an immunoassay where agglutination or precipitation reactions are inhibited, and the "hook effect" where conditions of antigen excess result in falsely low results. Conditions where the prozone effects occur can result in false negatives and falsely low results with catastrophic results to the patient.

Each assay combination has an empirically defined working range and assays must be performed with samples and reactants in the appropriate dilutions. This type of dilution has traditionally been accomplished through the use of precision fluid-handling components or manual repeating of the assay at higher dilutions of the antibody to see if the negative is a true negative. Although these can be very accurate, they require careful calibration and greatly add to the complexity of automated instrumentation. Additionally the range of analyte present in the sample may exceed the dynamic range of the assay and may require further dilution of the sample for accurate results. Additionally, the prior art requires many chambers to contain the various concentrations of reactants.

Serologic assays, such as for antibodies to infectious disease pathogens, are important in that they tell of either existing immunity due to immunization or to previous or current exposure, depending on the class of immunoglobulin present, to the infectious agent. Similarly, they may be used to detect auto-immunity and the like. There are a number of assay types performed, including agglutination, complement-fixation, precipitation, etc. One almost universal feature of such tests is the need to dilute the sample a number of times in order to detect the point where the antibodies are no longer effective to cause a positive test. This is referred to as the "titer", the titer being the highest dilution of the patient's serum or plasma that yields detectable agglutination or measured reaction with the test antigen. This, in effect, requires the performance of many separate tests in separate chambers to arrive at the result. Another problem with such assays is that the endpoints are sometimes difficult to determine, thus adding a significant error to the titer determination. Automation can increase the test efficiency and accuracy, but performing the dilutions by an instrument is very difficult and time consuming including the need to first define the desired dilution which can vary from test to test and the multiple dilution steps are very complex.

It would be desirable to provide a method and apparatus for measuring antibody titers in an automated system which does not require multiple dilutions and that removes the risk of false negatives due to the prozone effect.

SUMMARY OF THE INVENTION

According to an aspect of the present invention, a sensible marker is used to permit the measurement of the concentration of the reactants added to the in vitro chamber in the area of the reaction being analyzed. A sensible marker in this disclosure means a dye or detectable substance that does not interfere with the reaction being analyzed and that diffuses at a rate close the reactants to which it is added. Sensible markers may be a dye or dyes that can be measured by optical means such as absorption or fluorescent emission. The sensible marker is homogeneously present either being in solution or colloidal suspension with at least one of two or more liquids to be subsequently added to, and allowed to mix in, the thin analysis chamber being used.

Since the height of the chamber is less than 100 microns (100% L), and preferable less than 20 microns (20 µl), and the lateral dimensions of the chamber are preferably several centimeters, the greater than 1,000 fold difference in the vertical and horizontal dimensions will result in equilibrium being reached in the vertical dimension extremely rapidly while the equilibrium in the lateral dimension will take hundreds to thousands of times longer. If the entire image of the reaction chamber imaged or scanned and discrete small areas of the image or scan are analyzed, where the lateral aspects of the discrete analysis areas are in the range of 1 to 3 times the height or the chamber, the volume being subjected to the analysis will be in approximate equilibrium. Areas taken at millimeter distances or greater, lateral to the first area will have different equilibrium conditions. The signal from the admixed sensible marker is measured before and after subsequent mixing or diffusion with the additional reactants, to permit calculation of final measured sensible marker concentration reflects the relative dilution of the components. In cases where there are more than two liquids present in a chamber, more than one sensible marker that is able to be distinguished from the other sensible markers may be employed, each added to one of the added components, to enable the calculation of relative proportions of each of the components. If the initial concentration of the constituents of the components is known, the relative concentrations may be used to calculate the absolute concentration of the added components in mass per unit volume. Thus, the relative concentrations of added reactants in any small analyzed area may be treated as a virtual discrete reaction vessel or chamber whose concentrations of added reagents is calculable and the results for the bound over free or agglutination or other signal employed in the immunoassay being performed may be measured and plotted as the signal obtained per calculated dilution of sample or standard per concentration of added antibody or added antigen.

It is therefore an object of this invention to provide a method and apparatus wherein mixing and diffusion are used to create a concentration gradient between two or more miscible liquids in a thin film sample in a chamber so that the equilibrium in the thin dimension of the chamber is very rapid and concentration differences in the long axis of the chamber do not reach equilibrium during the time of the assay, and the final relative inter-dilution being measured by the relative concentration of a sensible marker which does not participate in any of the desired chemical reactions and whose properties are such that it allows its accurate measurement at any small area in the reaction chamber.

DESCRIPTION OF THE DRAWINGS

FIG. 1 is a schematic plan view of a chamber which is used in the performance of the method of this invention.

FIG. 2 is a cross sectional view of the chamber of FIG. 1.

FIG. 3 is an enlarged cross sectional view of the chamber of FIG. 1 showing a pumping of the solution in the chamber by deflection of the top surface of the chamber to facilitate the establishment of different concentrations throughout the lateral aspects of the chamber.

FIG. 4 is a plan view of the chamber of FIG. 1 after the pumping step has been completed.

FIG. 5 shows a trace of fluorescent emission readings from the chamber of FIG. 1 as taken along line a-a of FIG. 4 where a sensible marker is a fluorescent dye.

FIG. 6 is a plan view of the chamber of FIG. 1 wherein the chamber has internal baffles which will cause sample mixing when the sample is first introduced into the chamber whereby physical manipulation of the sample is not needed.

FIG. 7 is a schematic plan view similar to FIG. 1, but with a relatively small sample in the chamber.

FIG. 8 is a plan view similar to FIG. 7 but showing the sample after mixing.

FIG. 9 is a schematic plan view of the chamber of FIG. 1 but showing the result of adding three liquids to the chamber.

DETAILED DESCRIPTION OF THE INVENTION

Figure 10:
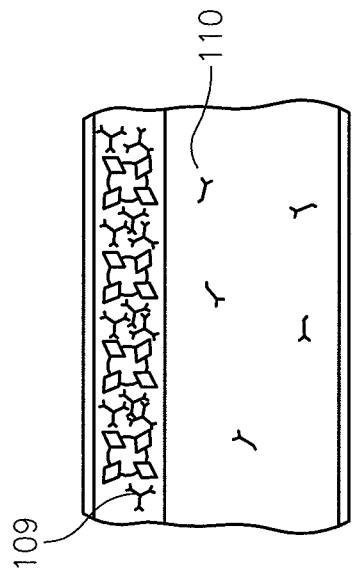
FIG. 10 is a schematic cross sectional view of a test chamber formed in accordance with this invention.

FIG. 1 is a schematic top view of a chamber 1, in this instance a square, whose cross-section is shown in FIG. 2. The chamber is comprised of relatively thin top and bottom plates, at least one of which must be transparent. Into the chamber are introduced two or more liquids, one being the sample 3 to be analyzed and the other being the reagent 4 required for the analysis. At least one of these liquids has a dissolved marker which may be fluorescent, such as fluorescence, or an absorbent dye, such as phenol red, or the like. The marker must be such that it does not chemically interfere with the desired analytical signal nor should the marker signal be affected by any signal or reaction products of the analysis in a manner, which cannot be compensated for.

In the instance shown, liquid 4 is the analyzing reagent which contains a fluorescent marker, and liquid 3 is the sample to be analyzed. If the liquids are introduced into the chamber in equal amounts, in the directions indicated, they will meet approximately at region 5. FIG. 3, which is also an enlarged cross-sectional view of the chamber, demonstrates how the liquids may be partially mixed. If one of the chamber surfaces is "pumped" up and down, mixing of the liquids will occur, approximately along line 6, resulting in the dilution gradient shown in FIG. 4, which is a top view of the chamber.

After a suitable period of mixing, the chamber is allowed to stand for a period of time sufficient to allow vertical diffusion to complete the mixing the liquids within a given vertical segment. At this point, the fluids in regions 7 and 8 are still completely undiluted and represent the native state of the liquids before mixing. If fluorescence readings from the marker are then taken along line a-a, the result can be seen in FIG. 5, which is a cross-sectional view of the chamber along line a-a, with a superimposed graph showing the fluorescence of the chamber at each relative position and a second graph showing the optical absorbance from the analyte.

Since signal level 9 represents that from the undiluted markered reagent, and signal level 10 represents the background level of the sample, the chamber region corresponding to signal level 11 contains a sample which has been diluted exactly by half. Thus, the analyte concentration inferred from the signal of the desired reaction may be multiplied by two to obtain the exact concentration. If, in this instance, it is known that the analyte signal is too high due to the presence of too much analyte in the mixture in that region, one need only find a region with a marker signal equivalent to that of region 12, which is a greater dilution, and then multiply the analyte absorbance result accordingly.

Similarly, in conditions where the prozone effect is present, the instrument reports the highest analyte result obtained after taking all dilutions into account and also reports that this calculation has been performed.

The sample may be mixed by other means then "pumping" the chamber. For example, FIG. 6 is a schematic top view of a chamber with baffles 13 which serve to cause sample mixing when the liquids are introduced as shown.

It is not necessary for some portion of either the sample or the reagent to remain undiluted. For example, in FIG. 7, which is another schematic top view of a chamber with a relatively small sample 14, where in this case the sample is the liquid containing the marker, and a large reagent area 15 which does not contain the marker. Prior to mixing, reference readings are taken over regions 16 and 17, and after mixing (FIG. 8), there is no remaining undiluted sample, but the original reference values can be used for the same calculations as described above. This particular instance, where a marker is uniformly mixed with the sample, is particularly suited for instances where a relatively high dilution ratio is required.

All of the instances shown show the formation of a dilution gradient, but this may not always be necessary. In cases where a single, approximate dilution will suffice, the sample and markered reagent (or markered sample) can be mixed to uniformity and a reading taken from any suitable region, again using the marker concentration to calculate the final actual dilution.

In the above instances, it was assumed that the thickness of the chamber was uniform, but this is not absolutely required. It would be acceptable to a chamber having a thickness at the point of measurement that is known or can be determined from other means; e.g., the absolute reading position in the case of a chamber of defined geometric shape, or a thickness that can measured by means independent of the marker, such as interferometry or by the systems described in U.S. Pat. Nos. 6,127,184, 6,723,290 and 6,929,953, which patents are hereby incorporated by reference in their entirety.

The chamber thickness must be sufficiently small that convection cells do not develop, and also small enough that complete vertical mixing by diffusion can occur in a reasonable period of time. In the preferred embodiment, the chamber is less than 1 mm thick, and preferably less than 200μ. The area of the chamber is largely irrelevant, but for most applications an area of about 4 cm$^2$ is adequate.

In instances where the chamber must be incubated for a prolonged time following mixing in order for a reaction to proceed, the gradient may tend to decrease due to diffusion beyond desired bounds. In these cases, a viscosity increasing agent, such as dextran, polyoxyethylene or the like, or by an agent which can form at least a partial gel, such as gelatin or agar, can be used to delay further diffusion.

An additional particularly important application of this invention is the means by which it can be used to provide a simultaneous standard curve and analytical dilution. Standard curves are frequently used to calibrate a given analysis, where known standards of varying concentrations are analyzed to generate a response curve of analytical signal vs. sample concentration. When the sample containing the unknown concentration of analyte is then measured, the analytical signal is compared to the standard curve to give the concentration of the analyte in the sample. This necessitates multiple analyses in separate vessels, and if the reaction is not repeatable over time, this may require a repetition of this process with every analytical run. A similar situation exists with the use of control material, which is, in effect, standards of known concentration, which are analyzed along with the sample in a batch in order to ensure that the analysis is working properly. Both of these situations can be avoided by a particular use of the described invention.

FIG. 9 shows a sample cell 18 where three liquids are introduced, the sample containing the unknown concentration of analyte, the reagent containing the marker, and a standard of appropriate concentration. Baffles 19 may be used to prevent complete mixing of the constituents. When the chamber has equilibrated as previously described, readings along line 21 are used to generate a standard curve, using the previously described method, and readings along line 20 are used to find the appropriate sample dilution for the analysis. Thus, a simultaneous standard curve and sample analysis can be performed in the same reaction chamber, which ensures that the reaction conditions for the sample and standard are identical. More than one sample could be run in a single chamber by altering the geometry, as long as the appropriate mixing occurs. What is being measured is light per pixel of the area scanned.

An agglutination assay is performed in the test chamber as described above, with the following features added to affect a serologic assay. Preferably, control particles, similar in chemical composition to the particles expressing the target epitope, but lacking the target epitope, will be present in the sample along with the target particles. The control particles are distinguishable by their color or other features from the particles containing the target epitope so that ligand-induced agglomeration of the control particles should not normally occur. If significant agglutination of the control particles does occur, this indicates non-specific agglutination and this condition may be used to ascertain the validity of the test. For example, if 50% of the target epitope-containing particles are agglutinated, and less than 10% of the control particles are agglutinated, this would indicate a positive test. If equal significant numbers of control and target epitope-containing particles are agglutinated, the test is invalid. When there is no significant agglutination of either the targets or the controls that means that the target antigen which is specific to the target epitope is not present in the sample being tested. This result is also considered to be a valid test of a negative result.

FIG. 10 is a schematic cross-sectional view of a test chamber having at least one transparent surface 101 of the general construction described above. To one surface of the chamber are adhered first particles 102 whose surfaces express or contain the antigen 103 to which the target antibody is directed. The particles may be artificial, such as latex, latex-styrene, styrene, polycarbonate, or the like, with antigen bonded to the surface by any of several means well known to the art, or they may be natural, such as pollen, bacteria, yeast, mold or fungus. The particles must be of such a size so as to enable the determination that particle agglutination has occurred, and are most preferably in a size range of 0.2μ to 20 μ. The particles are adhered to, and preferably covered by, a soluble coat 104, which may be comprised of sugars, such as trehalose, which preserves the activity of the antigen 103. Also present in the test chamber are control particles 115 which have surface antigens 114 to which the target antibody is not directed. The control particles 115 are in the same size range as the first particles 102 and are preferably formed from the same materials as the first particles 102.

Figure 11:
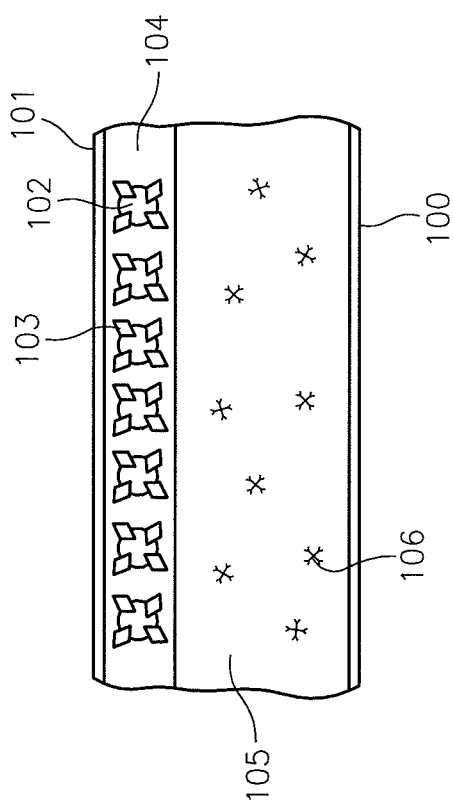
FIG. 11 is a view of the test chamber similar to FIG. 10, showing agglutination of target epitope-containing particles after adding a test sample to the chamber and the absence of agglutination of control particles.

When a liquid sample 105 containing the antibodies to be detected 106 is added to the chamber, the soluble coat 104 dissolves, releasing the first particles 102 and the control particles 115 and exposing the adhered antigen 103 to the antibody 106 (if present in the sample). As shown in FIG. 11, which shows the chamber of FIG. 10 some time after the sample has been added, the antibody 106 in the sample, if present in sufficient quantity, will cause the first particles 102 to agglutinate to form at least pairs of particles 107, or if present in higher concentration, to form larger clumps 108. It is readily apparent that inspection of the chamber by an automated instrument can detect the presence of clumping of the particles by any number of image-processing algorithms well known to the art. In the example illustrated in FIG. 11, the control particles 115 are not agglutinated or clumped together.

Figure 12:
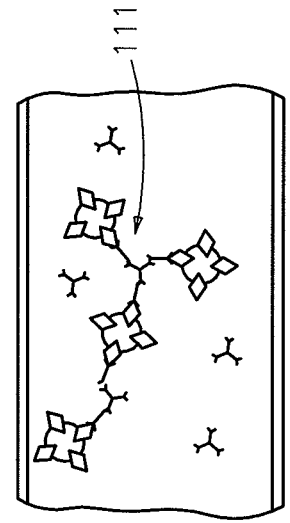
FIG. 12 is a cross sectional view similar to FIG. 10 showing antibodies present in the test chamber before the test sample is added to the chamber.
Figure 13:
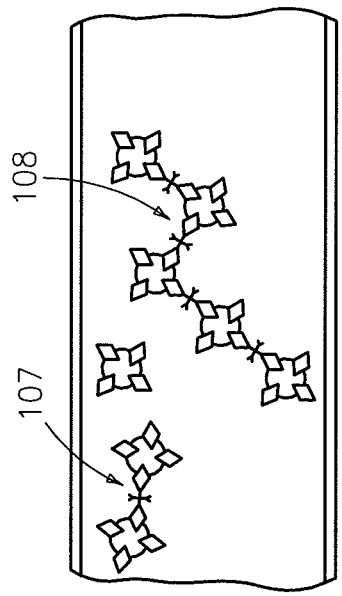
FIG. 13 is a view similar to FIG. 11 showing agglutination of target epitope-containing particles after adding a test sample to the chamber and the absence of agglutination of control particles.

In the example given, the antibody 106 was presumed to be polyvalent, such as Ig-M, which is the antibody formed in the early stages of a response to an infection. If the immune response is longer lasting, however, Ig-G antibody will be present, which is not polyvalent and is less effective in causing the clumping. To effect a better clumping in that case, the soluble layer 104 should contain a polyvalent anti-Fc antibody active to link the Fc fragments of the non-polyvalent antibody 110 to be detected. Thus, when layer 104 dissolves, the anti-Fc antibody 109 is released and binds the antibodies 110, in effect, creating a form of polyvalent antibody 110 which can clump the particles 102 as shown in FIGS. 12 and 13.

Figure 14A:
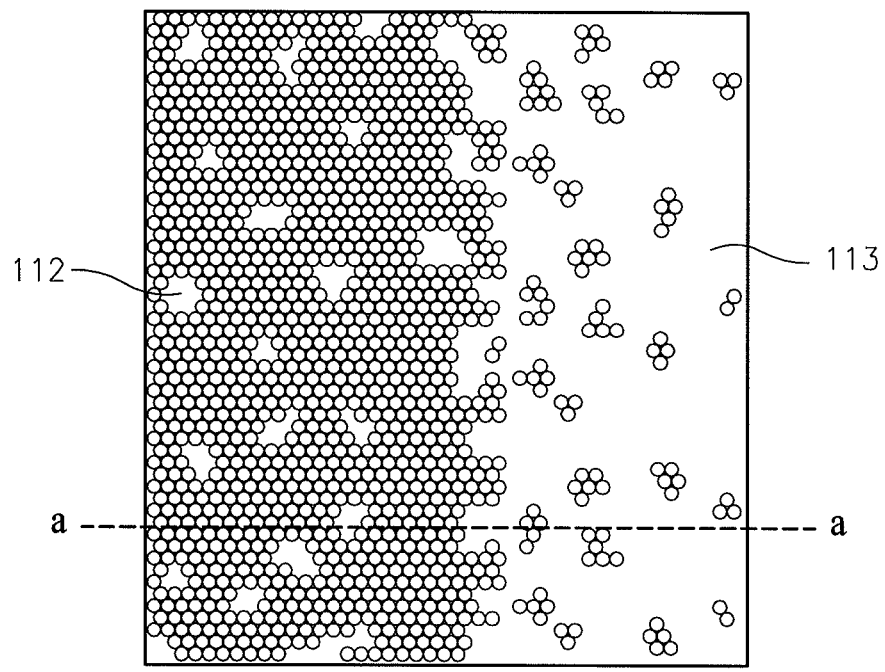
FIG. 14A is a compound plan view of a test chamber which shows the presence of agglutinated target epitope-containing particles in the sample and the absence of agglutination of control particles.
Figure 14B:
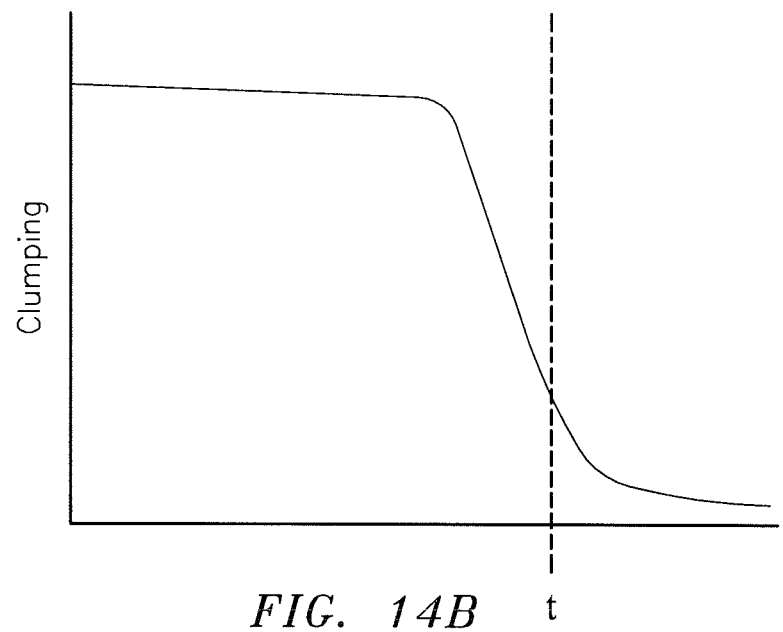
FIG. 14B is a graph of the agglutinated particles in the sample taken from a scan along line a-a, and showing the cut off location T of the absence of particle agglutination in the sample.

FIGS. 14A and 14B are schematic top views of chambers combining the features of the above-cited disclosure and the instant disclosure, and a graph depicting the presence of aggregated particles versus the position along line a-a, respectively. Sample 112, admixed with a marker as previously described, and a diluent 113 is introduced into a chamber in a manner so as to allow the formation of a gradient dilution. After a suitable incubation period which will depend upon the nature of the antigen and antibody being detected, the chamber is scanned along line a-a and the region T is located, as seen in FIG. 14B, which represents the position where agglutination or clumping no longer occurs. The reciprocal of the dilution of the sample at this point, as determined by the relative concentration of the marker in this area, is equal to the titer of the antibody. For example, if the marker concentration is 0.2 compared to that in the original sample area 112, the titer is 5. Non-agglutinated control particles 115 are also shown in FIG. 14A.

It should be noted that other immunological reactions besides agglutination or clumping can be detected, such as precipitation, where the antigen and antibodies form a visible complex instead of clumping particles. It should also be noted that the means described in the present invention may also be employed in other types of immunoassays, including those where the method of analysis includes the virtual subtraction off bound from free, the subject of the copending U.S. Provisional Patent Application No. 61/041,784, filed Apr. 2, 2008 and Docket No. 7564-0035-1, filed presently herewith. In the latter case, with the present invention there is no need to avoid prozone effects, but the present invention can be used to optimize the working range on the assay and may be performed without deviation from the specifications contained in the present disclosure.

Although the invention has been shown and described with respect to specific detailed embodiments thereof, it will be understood by those skilled in the art that various changes in form and detail thereof may be made without departing from the spirit and the scope of the invention.

What is claimed is:

1. A method for performing a serologic agglutination assay for one or more target analyte antibodies in a liquid sample, said method comprising the steps of:
   a) providing a thin planar chamber having opposed planar surfaces, at least one of which is transparent, which chamber has a height that is equal to or less than 20 μm;
   b) placing an effective amount of detectable first particles in said planar chamber, said first particles containing on their surfaces an antigen against which the target analyte antibodies are directed;
   c) placing control particles, similar in size and shape to said first particles, in said chamber, said control particles differing from said first particles in color, and said control particles being devoid of said antigens, and disposing a volume of sample within the thin planar chamber such that at least a portion of the sample contacts both opposed planar surfaces of the chamber;
   d) allowing or causing said detectable first particles and said sample to admix with each other whereby said target analyte antibodies, when present, will cause agglutination of said detectable first particles;
   e) electronically imaging or scanning said admixture to detect individual aggregates of particles by analysis of patterns of pixel intensity resulting from aggregation of detected particles; and
   f) determining the presence or absence of significant particle agglutination by comparing signals of any aggregated first particles with signals of any aggregated control particles.

2. The method of claim 1 wherein the detection of presence of agglutination of particles is performed by measuring pixel areas of agglutinated first particles with pixel areas containing any agglutinated control particles.

3. The method of claim 1 wherein the detection of agglutination of particles is performed by determining the percentage of particles of any given type that are aggregated or clumped.

4. The method of claim 1 wherein there are more than one class of separately distinguishable detectable first particles, each class containing different antigens so that multiple assays may be simultaneously performed in the same sample chamber.

5. The method of claim 1 wherein said first particles and said control particles are differentially marked so as to be distinguishable one from the other.

* * * * *